United States Patent [19]

Kaufman et al.

[11] Patent Number: 5,148,944

[45] Date of Patent: Sep. 22, 1992

[54] INTERACTIVE MEDICATION DELIVERY SYSTEM FOR INDIVIDUAL PILLS AND CAPLETS

[75] Inventors: Stephen B. Kaufman, Highland Park; Aleandro DiGianfilippo, Crystal Lake; Tamara L. Sager, Libertyville, all of Ill.; Ralph J. DeVito, Stanhope, N.J.

[73] Assignee: Health Tech Services Corporation, Northbrook, Ill.

[21] Appl. No.: 414,921

[22] Filed: Sep. 29, 1989

[51] Int. Cl.$^5$ ............................................. B65G 59/00
[52] U.S. Cl. .................................. 221/131; 221/264; 221/268
[58] Field of Search ............... 221/268, 270, 133, 131, 221/124, 274, 272, 270, 129, 123, 263, 264, 111, 107, 108

[56] References Cited

U.S. PATENT DOCUMENTS

| | | | |
|---|---|---|---|
| 2,636,795 | 4/1953 | Williams | 221/131 |
| 3,351,233 | 11/1967 | Chanoch et al. | 221/131 |
| 3,369,697 | 2/1968 | Glucksman et al. | 221/9 |
| 3,395,829 | 8/1968 | Cogdell et al. | 221/15 |
| 3,545,164 | 12/1970 | Middleton | 221/264 |
| 3,651,984 | 3/1972 | Redenbach | 221/3 |
| 3,722,739 | 3/1973 | Blumberg | 221/3 |
| 3,762,601 | 10/1973 | McLaughlin | 221/2 |
| 3,815,780 | 1/1974 | Bauer | 221/5 |
| 3,857,383 | 12/1974 | Sommerfield et al. | 128/20 |
| 3,911,856 | 10/1975 | Ewing | 116/121 |
| 3,917,045 | 12/1975 | Williams et al. | 221/2 |
| 3,964,638 | 6/1976 | Diamauro | 221/3 |
| 3,968,900 | 7/1976 | Stambuk | 221/3 |
| 3,998,356 | 8/1976 | Christensen | 221/3 |
| 4,034,740 | 7/1977 | Atherton et al. | 128/113 |

(List continued on next page.)

OTHER PUBLICATIONS

Pending Patent Application (Ser. No. 07/201,779) filed Jun. 2, 1988; Kaufman et al.

Comarchero et al., "*A Micro-Computer Based System for the Management of the Critically Ill*", 1978.

Blum et al., "*Protocol Directed Patient Care Using a Computer*", (1980).

Rodhard et al., "*A Data Management Program to Assist with Home Monitoring of Blood Glucose and Self Adjustment of Insulin Dosage for Patent with Diabetes Mellitus and Their Physicians*", (1984).

Kouchoukos et al., "*Automated Patient Care Following Cardiac Surgery*", (1971).

Hudson et al., "*Microcomputer-Based Expert System for Clinical Decision-Making*", (1981).

Worthman et al., "*Quality Assessment in Emergency Medical Services Systems: The Criteria Mapping Method*", (1979).

Greenfield et al., "*The Clinical Investigation and Management of Chest Pain in an Emergency Department*", (1977).

Sander et al., "*Micro-Computer Controlled Care System for the Severly Physically Impaired*", (1984).

Primary Examiner—Robert P. Olszewski
Assistant Examiner—Kenneth Noland
Attorney, Agent, or Firm—Fuller, Ryan & Hohenfeldt

[57] ABSTRACT

A medication delivery device includes a housing that encloses a storage chamber for holding at least one pill/caplet. The housing also includes a dispensing chamber. The storage chamber has a first opening communicating with the dispensing chamber for conveying a pill/caplet from the storage chamber into the dispensing chamber. The dispensing chamber has a second opening for dispensing the pill/caplet from the housing. A shuttle member is movable within the dispensing chamber between a first and second position. The shuttle member has a delivery mechanism that receives a pill/caplet through the first opening as the shuttle member is moved from its first position toward its second position. The delivery mechanism carries the received pill/caplet to the second opening for dispensing as the shuttle member is returned to its first position.

8 Claims, 13 Drawing Sheets

U.S. PATENT DOCUMENTS

| | | | |
|---|---|---|---|
| 4,034,757 | 7/1977 | Glover | 128/260 |
| 4,130,881 | 12/1978 | Haessler et al. | 364/900 |
| 4,207,992 | 6/1980 | Brown | 221/15 |
| 4,223,801 | 9/1980 | Carlson | 221/3 |
| 4,227,526 | 7/1988 | Goss | 364/416 |
| 4,258,354 | 3/1981 | Carmon et al. | 340/309.4 |
| 4,275,384 | 6/1981 | Hicks et al. | 340/309.4 |
| 4,360,125 | 11/1982 | Martindale et al. | 221/2 |
| 4,361,408 | 11/1982 | Wirtschafter | 368/10 |
| 4,367,955 | 1/1983 | Ballew | 368/10 |
| 4,382,688 | 5/1983 | Machamer | 368/10 |
| 4,405,060 | 9/1983 | Hsei | 221/264 |
| 4,419,016 | 12/1983 | Zoltan | 368/10 |
| 4,448,541 | 5/1984 | Wirtschafter | 368/10 |
| 4,473,884 | 9/1984 | Behl | 364/479 |
| 4,483,626 | 11/1984 | Noble | 368/10 |
| 4,490,711 | 12/1984 | Johnston | 340/10 |
| 4,504,153 | 3/1985 | Schollmeyer et al. | 368/10 |
| 4,526,474 | 7/1985 | Simon | 368/10 |
| 4,572,403 | 2/1986 | Benaroya | 221/3 |
| 4,573,606 | 3/1986 | Lewis et al. | 221/3 |
| 4,616,316 | 10/1986 | Hanpeter et al. | 364/413 |
| 4,674,651 | 6/1987 | Scidmore et al. | 221/3 |
| 4,674,652 | 6/1987 | Aten et al. | 221/3 |
| 4,695,954 | 9/1987 | Rose et al. | 364/413 |
| 4,712,562 | 12/1987 | Ohayon et al. | 128/672 |
| 4,725,997 | 2/1988 | Urquhart et al. | 368/10 |
| 4,731,726 | 3/1988 | Allen | 364/416 |
| 4,775,077 | 10/1988 | Capotorto | 221/131 |
| 4,776,016 | 10/1988 | Hansen | 381/42 |
| 4,803,625 | 2/1989 | Fu et al. | 364/413.03 |

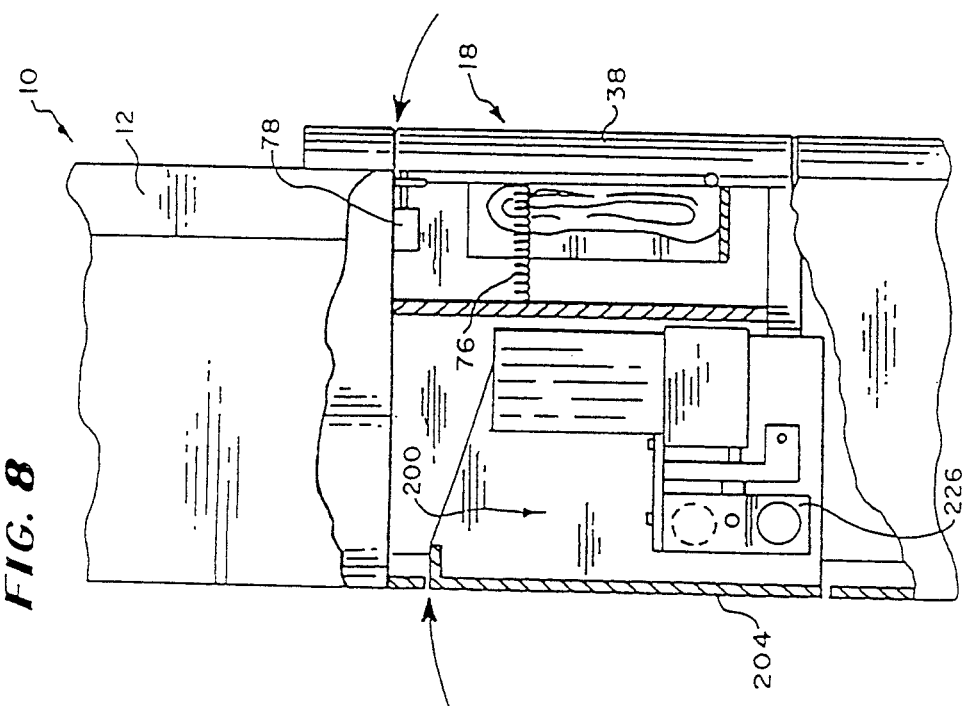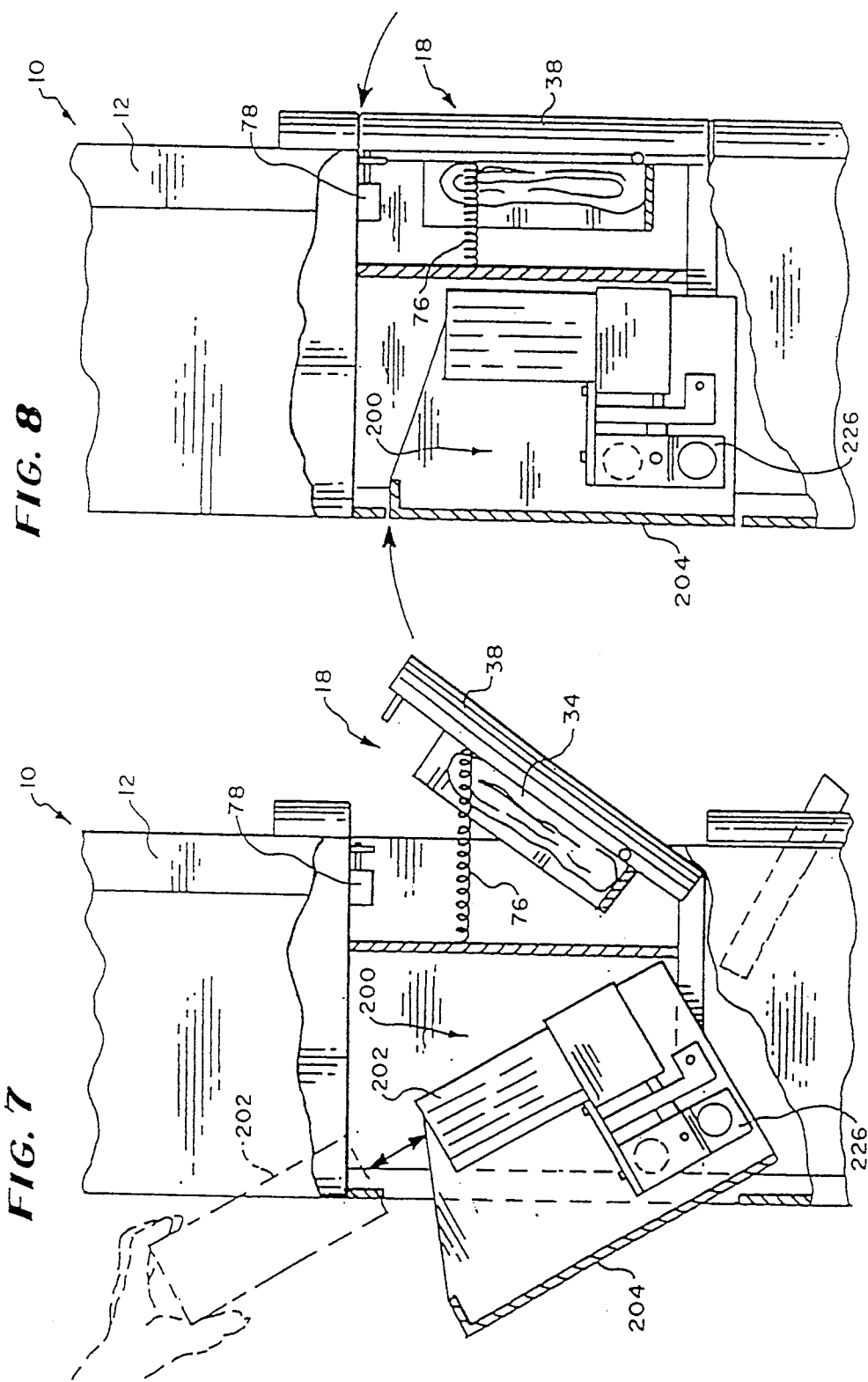

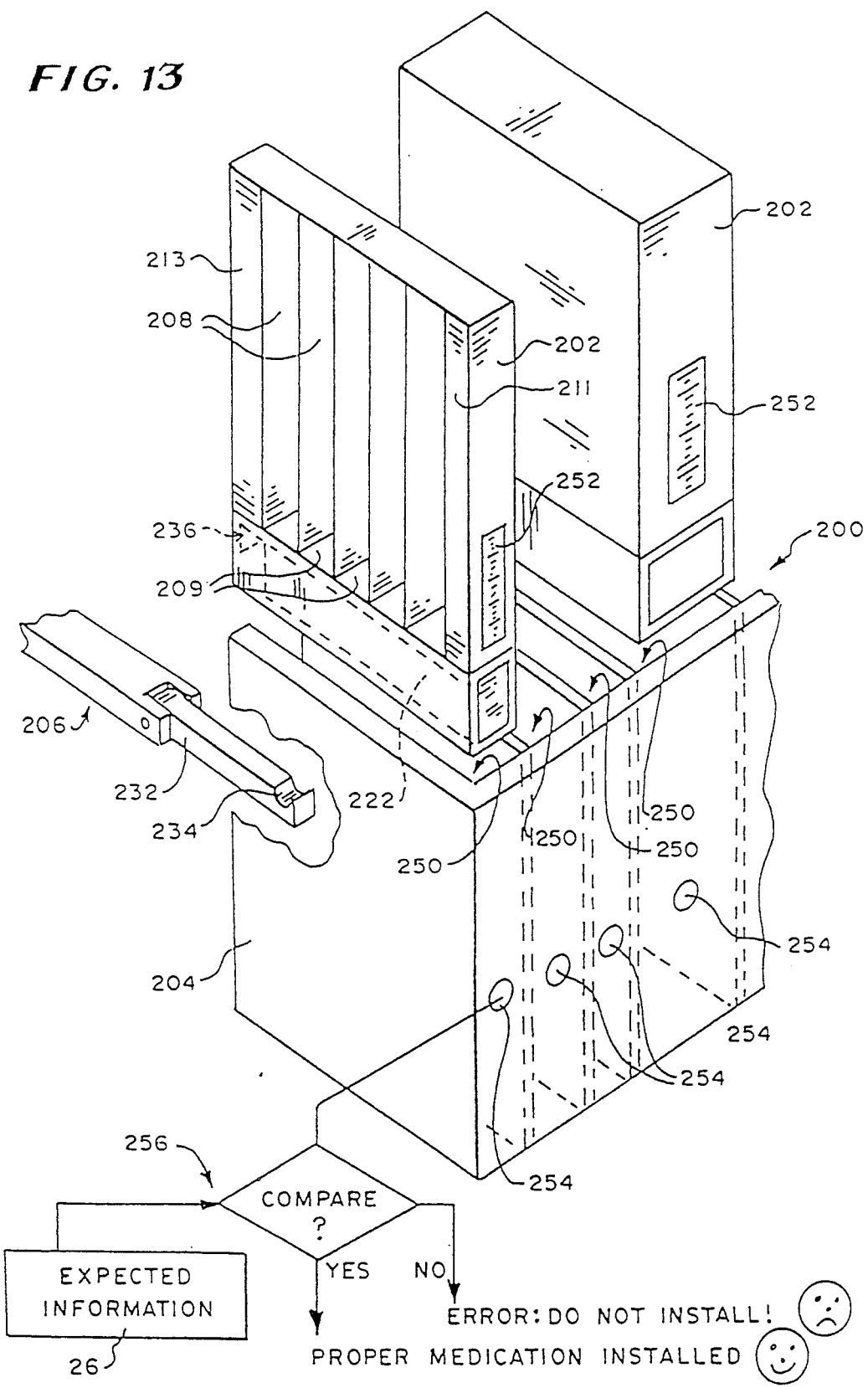

INTERACTIVE MEDICATION DELIVERY SYSTEM FOR INDIVIDUAL PILLS AND CAPLETS

FIELD OF THE INVENTION

The invention generally relates to systems for dispensing medications. In a more particular sense, the invention concerns systems which oversee and coordinate the administration of complex medication regimens at home, outside the support system of a hospital or pharmacy, and without the day to day supervision of medical personnel. In this more particular sense, the invention also concerns automated home care patient health monitoring systems.

BACKGROUND OF THE INVENTION

Due to advances in medicine and medical treatments in general, people are living longer. As a result, the number and percentage of older people are growing in the United States and elsewhere.

However, despite medical advances, many elderly people still face chronic and debilitating health problems. Arthritis, hypertension, and heart conditions are but a few examples of the problems associated with longevity.

Treatment of these health problems often requires close compliance with relatively complex medication regimes. It is not unusual for a person having one of the above health problems to be taking four or more different prescription drugs at one time. These drugs often differ significantly in dosages, both as to time and amount, as well as in their intended physiological effects. These drugs also often differ in the severity of potentially adverse reactions due to mismedication.

Close and careful compliance with these complex medication regimes is a difficult task in itself. The difficulty is greatly enhanced, considering that the elderly must discipline themselves to follow these regimes at home, without the day-to-day support and supervision of trained hospital and pharmacy personnel, and often without the day-to-day support and supervision of their immediate families or other caregivers. Furthermore, a loss in short term memory can be naturally attributed to the aging process and to the medication themselves, resulting in forgetfulness and further confusion in scheduling compliance with complicated medication regimes.

The elderly are therefore increasingly at risk of hospitalization or death from mismedication.

An interactive patient assistance device, ideally suited to the needs of home care patients—young and old alike—is described in Kaufman et al. U.S. patent application No. 201,779 (filed June 2, 1988). The device includes a self-contained medication delivery mechanism and self-contained physical testing apparatus. The device normally retains the medication and the testing apparatus away from access by the patient. Both medication and the testing apparatus are made available to the patient, either in response to a prescribed schedule or in response to a verbal command made by the patient.

The present invention enhances and expands the flexible, interactive system described in the Kaufman et al. application.

The invention is directed to improving the overall well-being and lifestyle of home care patients who are on complicated medication regimes. The invention addresses the problems of compliance with a complicated regime of differing medications and solves these problems by providing a reasonable degree of self-sufficiency and personal control over the administration of medication without sacrificing the overall therapeutic objectives of the prescribed medical treatment.

SUMMARY OF THE INVENTION

The invention provides a device and related systems for administering medication in the form of individual pills/caplets.

In one aspect, the invention provides a medication delivery device having a housing that encloses a storage chamber for holding at least one pill/caplet. The housing also includes a dispensing chamber. The storage chamber has a first opening communicating with the dispensing chamber for conveying a pill/caplet from the storage chamber into the dispensing chamber. The dispensing chamber has a second opening for dispensing the pill/caplet from the housing.

A shuttle member is movable within the dispensing chamber between a first and second position. The shuttle member has a delivery mechanism that receives a pill/caplet through the first opening as the shuttle member is moved from its first position toward its second position The delivery mechanism carries the received pill/caplet to the second opening for dispensing as the shuttle member is returned to its first position.

In a preferred embodiment, the delivery mechanism includes a passage that registers with the first opening to receive the pill/caplet when the shuttle member is in a predetermined position between the first and second positions. This passage also registers with the second opening to dispense the received pill/caplet from the passage when the shuttle member is in its first position In this arrangement, the delivery mechanism includes wall means adjacent the passage that blocks the first opening when the shuttle member is out of its predetermined position.

In a preferred embodiment, the storage chamber includes at least two separate storage compartments. Each of the compartments is capable of holding at least one pill/caplet and each has an associated first opening communicating with the dispensing chamber. In this arrangement, as the shuttle member is moved from its first position toward its second position, the delivery mechanism encounters one of the first openings before the other one of the first openings. The delivery mechanism receives the pill/caplet from the first encountered opening of a compartment that contains a pill/caplet. In this preferred arrangement, the passage receives only one pill/caplet as the shuttle member is moved between its first and second positions. The first received pill/caplet blocks the receipt of additional pills/caplets from subsequently encountered openings.

Another aspect of the invention provides a medication delivery system for individual pills/caplets in which at least two medication dispensing devices, as above described, are enclosed within a housing. Means is provided for independently actuating the shuttle member of each dispensing device. In this arrangement, each dispensing device can be selectively removed and replaced from the housing for replenishment and replacement purposes.

Another aspect of the invention provides a medication delivery system that includes separate first and second dispensing devices located within a housing. Each of the dispensing devices includes a compartment capability for storing at least one dose of a medication within the housing. A medication delivery mechanism is associated with each of the storage compartments for selectively delivering a medication dose from the associated storage compartment to the user. In this system, at least one of the dispensing devices contains medication in individual pill/caplet form and functions in the manner above described. A system control mechanism is provided for actuating the delivery mechanism associated with the first dispensing device in response to a first medication criteria and for actuating the delivery mechanism associated with the second dispensing device in response to a second medication criteria different from the first medication criteria.

Other features and advantages of the invention will become apparent upon reviewing the following detailed description, drawings, and appended claims.

BRIEF DESCRIPTION OF THE DRAWINGS

FIG. 7 is an enlarged side view, partially broken away, of the medication delivery system shown in FIG. 3, tipped outwardly from the rear of the associated patient assist device for replenishment of medication;

FIG. 8 is an enlarged side view, partially broken away, of the medication delivery system shown in FIG. 3 in its operative position within the associated patient assist device;

FIG. 13 is a perspective view, with portions in diagrammatic and schematic form, of the medication delivery system shown in FIG. 3.

DESCRIPTION OF THE PREFERRED EMBODIMENTS

Figure 1:
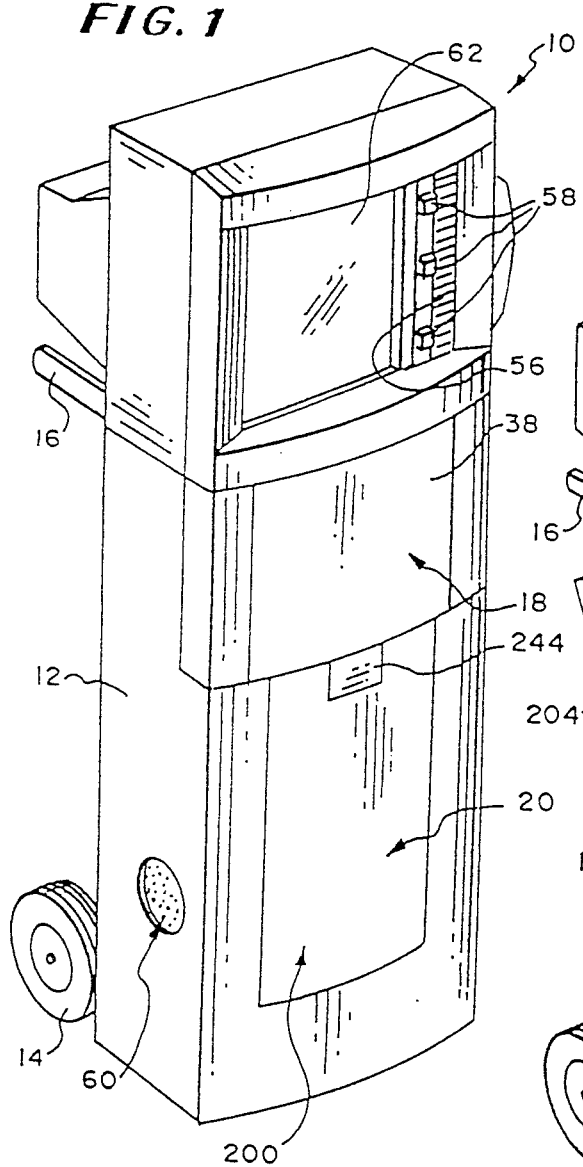
FIG. 1 is a front perspective view of a patient monitoring and assistance device having an enclosed system for delivering physical testing devices to the patient, as well as an enclosed medication storage and dispensing system that embodies the features of the invention for storing and dispensing medication in individual caplets, each of which systems is shown in its closed position.
Figure 2:
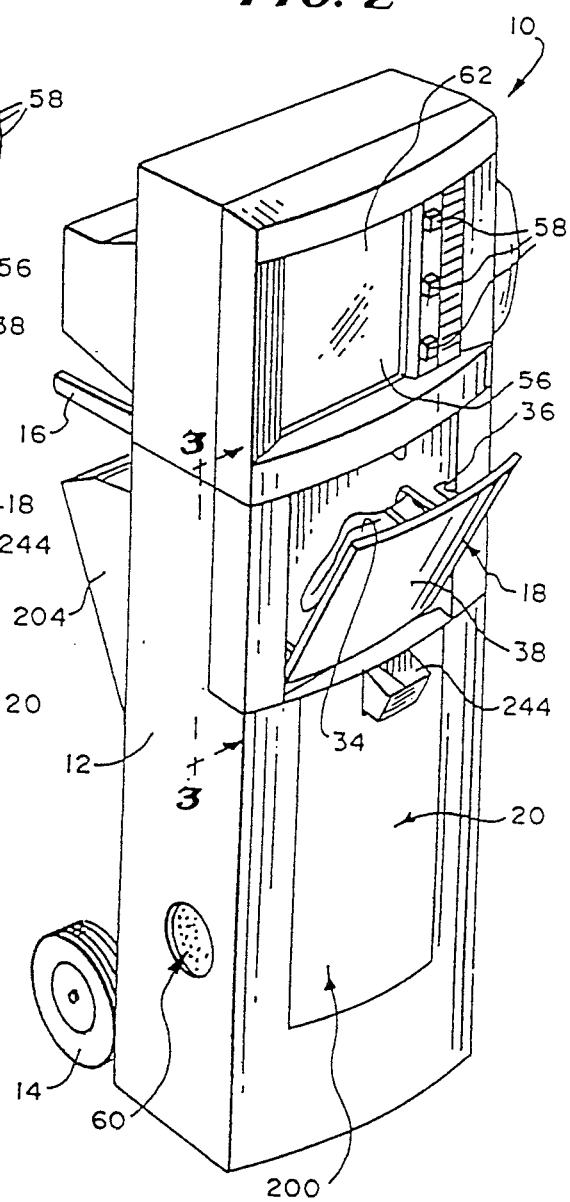
FIG. 2 is a front perspective view of the device shown in FIG. 1, with the testing device delivery system and medication delivery system each shown in its open position.

An interactive monitoring and assistance device 10 is shown in FIGS. 1 and 2. As will soon be described in greater detail, the device 10 performs as a self-contained, microprocessor-based caregiver who, in a friendly and supportive manner, monitors, manages and assists a patient in performing everyday health maintenance tasks. In carrying out its tasks, the device 10 monitors the patient's vital signs. The device 10 also stores and administers medication. The device 10 preferably is linked to a central facility that provides round-the-clock supervision and response as required.

The device 10 includes a housing or cabinet 12 that, in a preferred design, stands about four feet tall. Preferably, the housing 12 is portable. For this purpose, the device 10 includes wheels 14 and a handle 16 for the patient, or another user, to guide the movement.

As shown in FIGS. 1 and 2, the device 10 houses a system 18 for storing and delivering one or more devices for testing the vital signals of a patient. The device 10 also houses a system 20 for storing and administering medication (see FIG. 3 also).

Figure 4A:
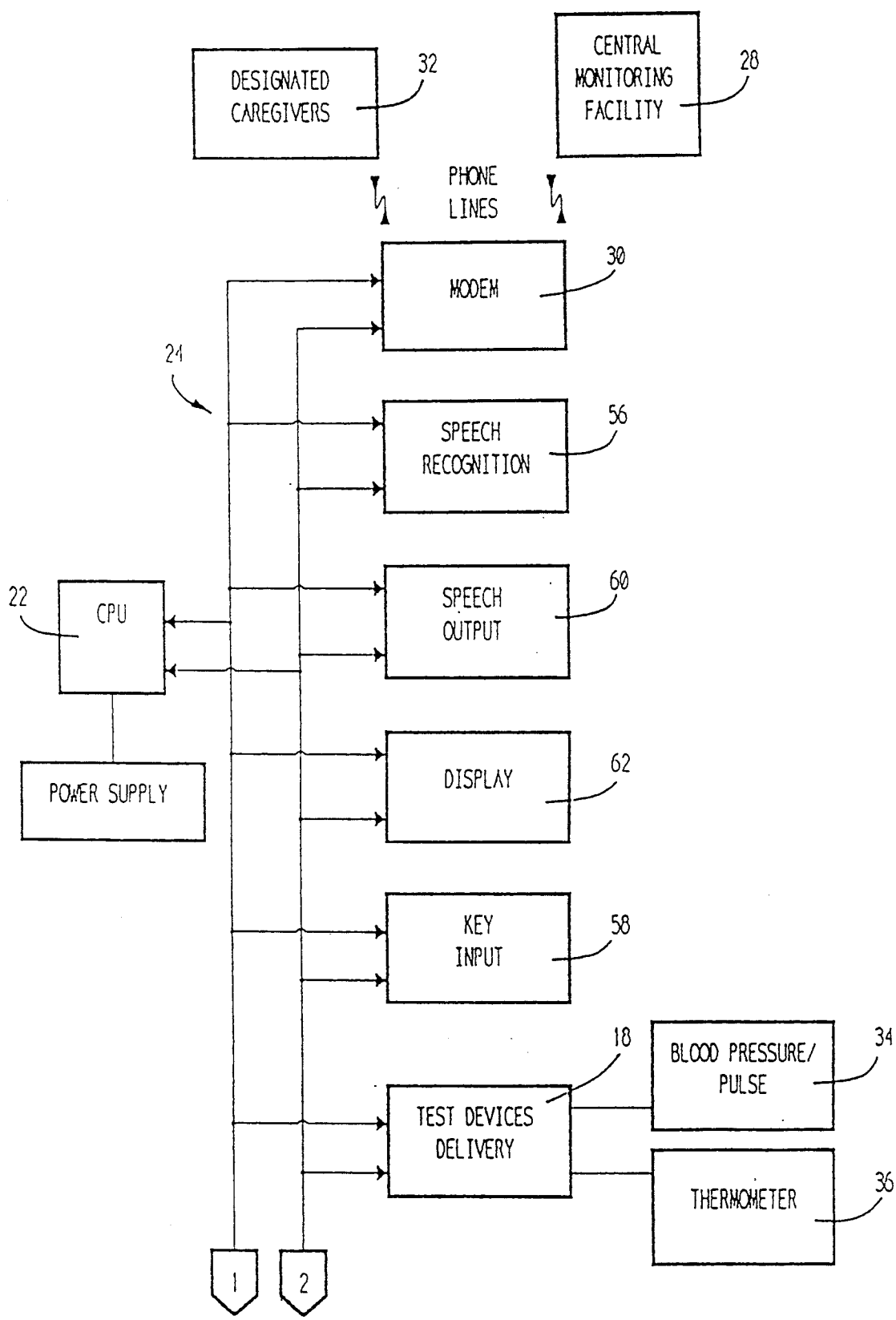
FIG. 4a and 4b are schematic block diagrams of the system that controls the operation of the patient assist device shown in FIG. 1.
Figure 4B:
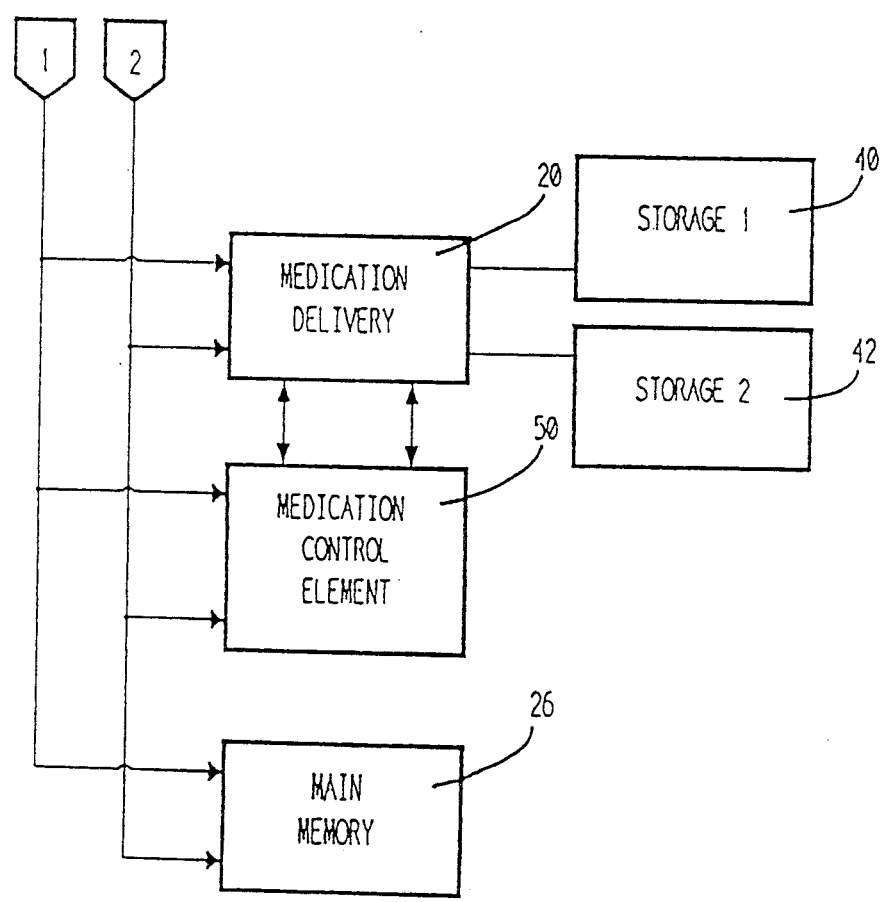

In the illustrated and preferred embodiment shown in FIG. 4, the device 10 houses a main microprocessor-based CPU 22 that coordinates and controls its operation. While various arrangements are possible, the CPU 22 preferably comprises an IBM PC compatible CPU board that accommodates multi-tasking sequences. Various input/output (I/O) devices communicate with the main CPU 22 through conventional data and address busses 24. The I/O devices will be described in greater detail later. A mass storage device 26 for storing digital information also communicates with the main CPU 22 through the busses 24.

In use, as shown in FIG. 4, the device 10 is preferably linked with a central monitoring facility 28 by a modem 30 that communicates with the main CPU 22 through the busses 24. Health care professionals are present on a twenty-four hour basis at the central facility 28 to monitor the health of the patient based upon information collected and transmitted to them by the device 10. The device 10 is also preferably linked via the modem 30 with selected individuals 32—typically close friends, family members, or other designated caregivers—who are automatically notified by the device 10 when certain health conditions exist or upon request by the patient or central facility 28. As can be seen, the device 10 is a central part of an overall support system for the patient.

As shown in FIG. 2, the system 18 for monitoring the patient's vital signs includes two physical testing devices: a pressure cuff 34 for measuring blood pressure and pulse rate, and a thermometer 36 for measuring body temperature. Of course, other testing devices could be provided, depending upon the health condition of the patient and mode of treatment.

As shown in FIG. 4, the testing devices 34 and 36 communicate with the main CP 22 through the busses 24. The measurements taken are stored in the data storage device 26. These measurements are also periodically transmitted to the central monitoring facility 28 by the modem 30. The central facility 28 also preferably records received information in its own mass storage device for record keeping, retrieval and analysis.

Preferably, the testing devices 34 and 36 are housed in a movable compartment or drawer 38 within the housing 12. The drawer 38 is normally closed (as shown in FIG. 1), thereby retaining the testing devices 34 and 36 within the housing 12 away from access by the patient. The drawer 38 will open in response to an appropriate command signal received and interpreted by the main CPU 22. The opened position for the drawer 38 is shown in FIG. 2. The testing devices 34 and 36 are thereby made available for use by the patient. This particular operation will be described in greater detail later.

The medication delivery system 20 housed within the device 10 (see FIG. 3) embodies the features of the invention. The system 20 is capable of storing and administering different types of medications having different administration criteria. The criteria can differ in terms of prescribed dosage amount, prescribed frequency of administration, degree of accessibility to the patient, or various combinations of the above.

The medication delivery system 20 includes at least two discrete storage compartments or cassettes (generally designated 40 and 42 in FIG. 3) within the housing 12. Each storage compartment 40 and 42 is separate and self-contained. Each compartment 40 and 42 is capable of independently storing at least one dose of a medication 44 within the housing 12 away from access by the user.

The medication delivery system 20 further includes independent delivery means or mechanisms associated with each storage compartment 40 and 42. In the illustrated arrangement (see FIGS. 3 and 5), a first delivery mechanism 46 is associated with the first storage compartment 40 for selectively delivering a medication dose from there to the patient. A second delivery mechanism 48 is likewise associated with the second storage compartment 42 for selectively delivering a medication dose from there to patient.

The number of individual delivery systems provided corresponds with the number of individual medication storage compartments. The number of storage compartments can, of course, vary. Only two storage compartments and their associated delivery systems will be discussed.

The first and second delivery mechanisms 46 and 48 operate independently and in response to different administration criteria. For this purpose (in particular, see FIG. 5), the medication delivery system 20 includes a control means or element 50 associated with the first and second delivery mechanisms 46 and 48. In the illustrated and preferred embodiment, the control element 50 communicates with the main CPU 22 (see FIG. 4, too), either in the form of programmable random access memory (RAM) or as preprogrammed read only memory (ROM).

According to its programming, the control element 50 is capable of receiving and differentiating between at least two different prescribed inputs. Upon the receipt and interpretation a first prescribed input or combination of inputs, the control element 50 will generate a control signal 52 that actuates the first delivery mechanism 46. Upon receipt of the second prescribed input or combination of inputs different from the first input, the control element 50 will generate a control signal 54 that actuates the second delivery mechanism 48. The control element 50 will not actuate the first delivery mechanism 46 in response to the second prescribed input.

Because the first and second control signals 52 and 54 are generated in response to different prescribed input criteria, the medications stored in the two storage compartments 40 and 42 can be selectively administered differently.

Figure 5:
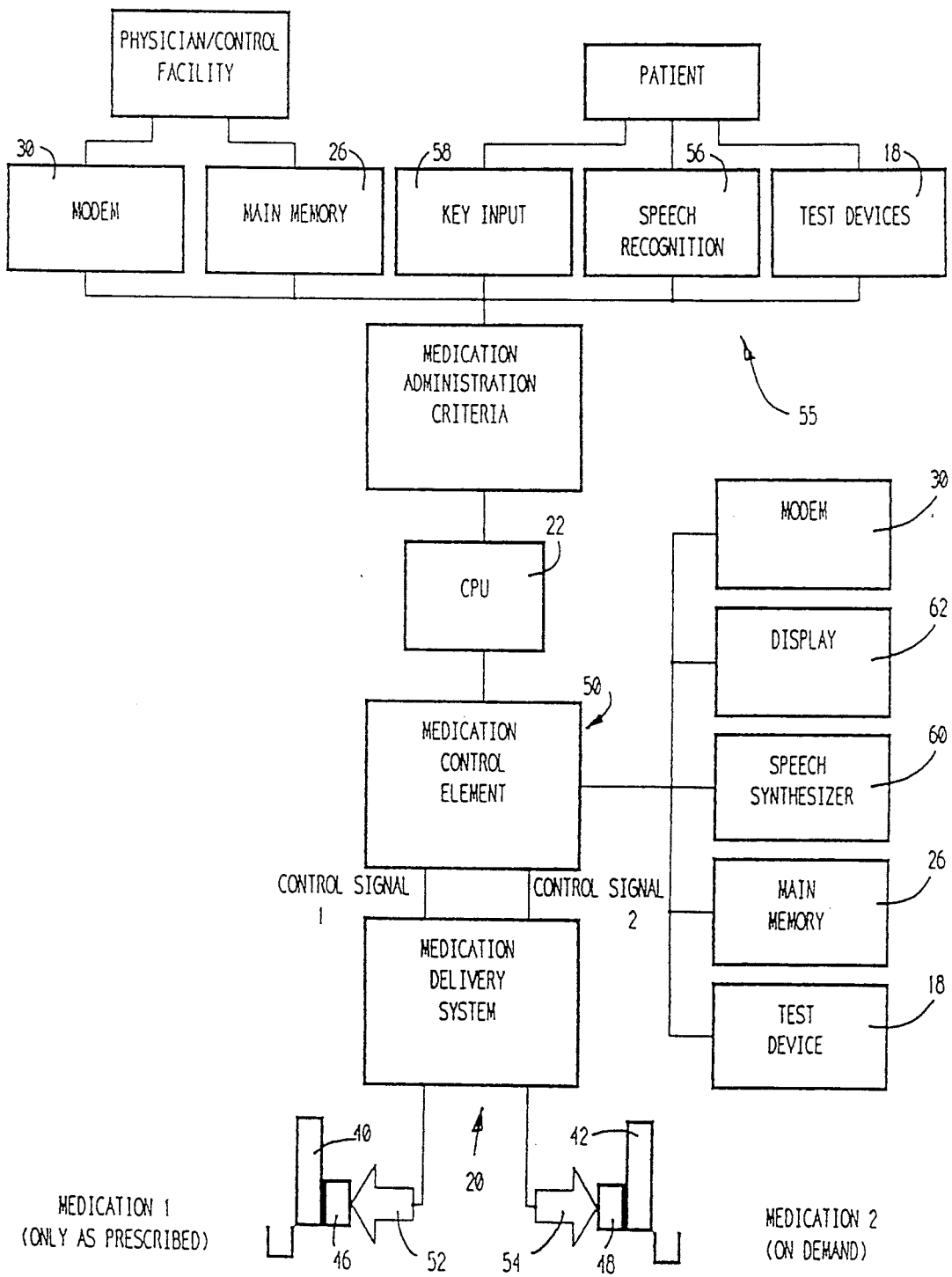
FIG. 5 is a schematic and partially diagrammatic block diagram of the elements of the system shown in FIG. 4 that control the operation of the medication delivery system that incorporates the invention.

As best shown in FIG. 5, the input criteria that generate the first and second control signals are derived from both external and internal devices 55 associated with the medication delivery system 20. These devices receive input from internal memory 26, the physician (or healthcare professional), and the individual patient.

More particularly, the system 20 includes in internal memory 26 one or more prescribed schedules for administering medication. Here, the attending physician records the medication regime he or she has prescribed for the patient.

The system 20 also includes various external input devices for receiving and interpreting prescribed commands either from the patient or from the central monitoring facility 28. These external input devices communicate with the control element 50 through the main CPU 22 (see FIG. 4). The received commands can include one or more specified commands for administering medication "upon demand".

In the illustrated and preferred embodiment shown in FIGS. 4 and 5, the external input devices include a speech recognition system 56 for receiving and interpreting preselected verbal commands made by the patient (for example, by using a Texas Instruments Recognition and Speech Unit Model TI-2245186-001). The external input devices also include the modem 30 for receiving and interpreting preselected commands from the central facility 28.

In addition, the external input devices preferably include one or more input buttons or keys 58 located at a user-convenient place on the housing 12. The keys 58 allow the patient to manually enter the prescribed medication delivery commands, if desired. In the illustrated and preferred embodiment shown in FIGS. 1 and 2, only a select few input keys 58 for entering block (or macro-) commands are provided. This arrangement simplifies the patient's interface with the device 10. However, it should be appreciated that a full keyboard could also be included, depending upon the degree of sophistication and desires of the patient.

In the illustrated and preferred embodiment shown in FIGS. 4 and 5, the system also includes an external output device associated with the main CPU 22 for delivering messages or otherwise communicating with the patient. Preferably, the external output device includes a speech generation system 60 for generating audible messages to the user. The speech generation system 60 can take the form of either a conventional device that synthesizes speech or a conventional device that digitizes prerecorded speech.

In addition, the external output device also preferably includes a video monitor 62 on which the audible messages appear in written form (see FIGS. 1 and 2 also). In this arrangement, the video monitor 62 can also display in written form the preselected medication administration commands. In this way, the video monitor 62 serves to visually back up and confirm the verbal messages and commands being exchanged by the patient and the device 10, thereby minimizing the chance of misunderstandings or failures to communicate.

Due to these various input and output devices, the medication delivery system 20 as just described affirmatively interacts with the patient, relying upon both spoken and written forms of communication with the patient.

For example, the control element 50 as above described can store and selectively administer one category of medication that should be administered only according to a prescribed schedule and another category of medication that can be administered upon demand by the patient.

Figure 6A:
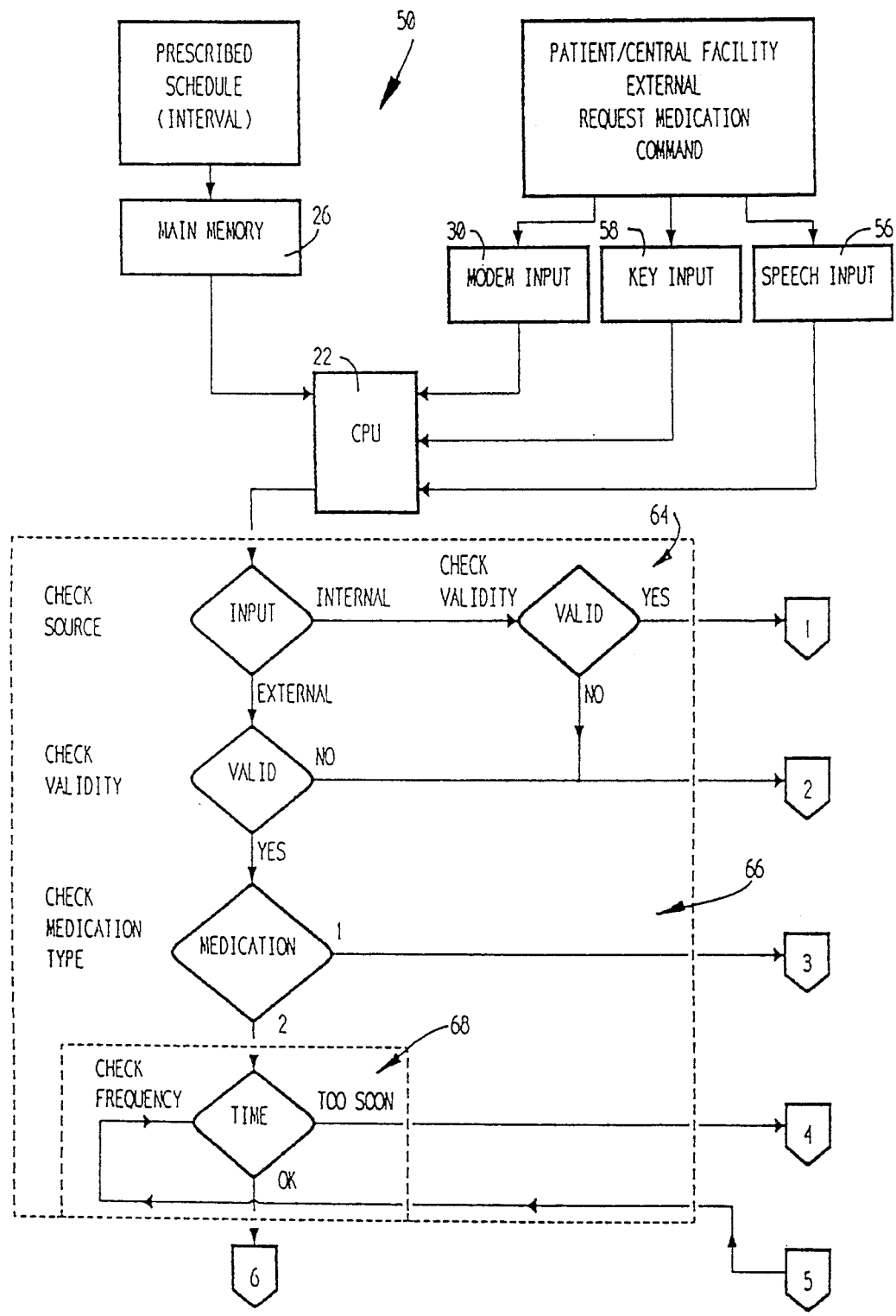
FIGS. 6a and 6b are schematic and partially diagrammatic flow chart of an embodiment of the system for controlling the operation of the medication delivery system that incorporate aspects of the invention.
Figure 6B:
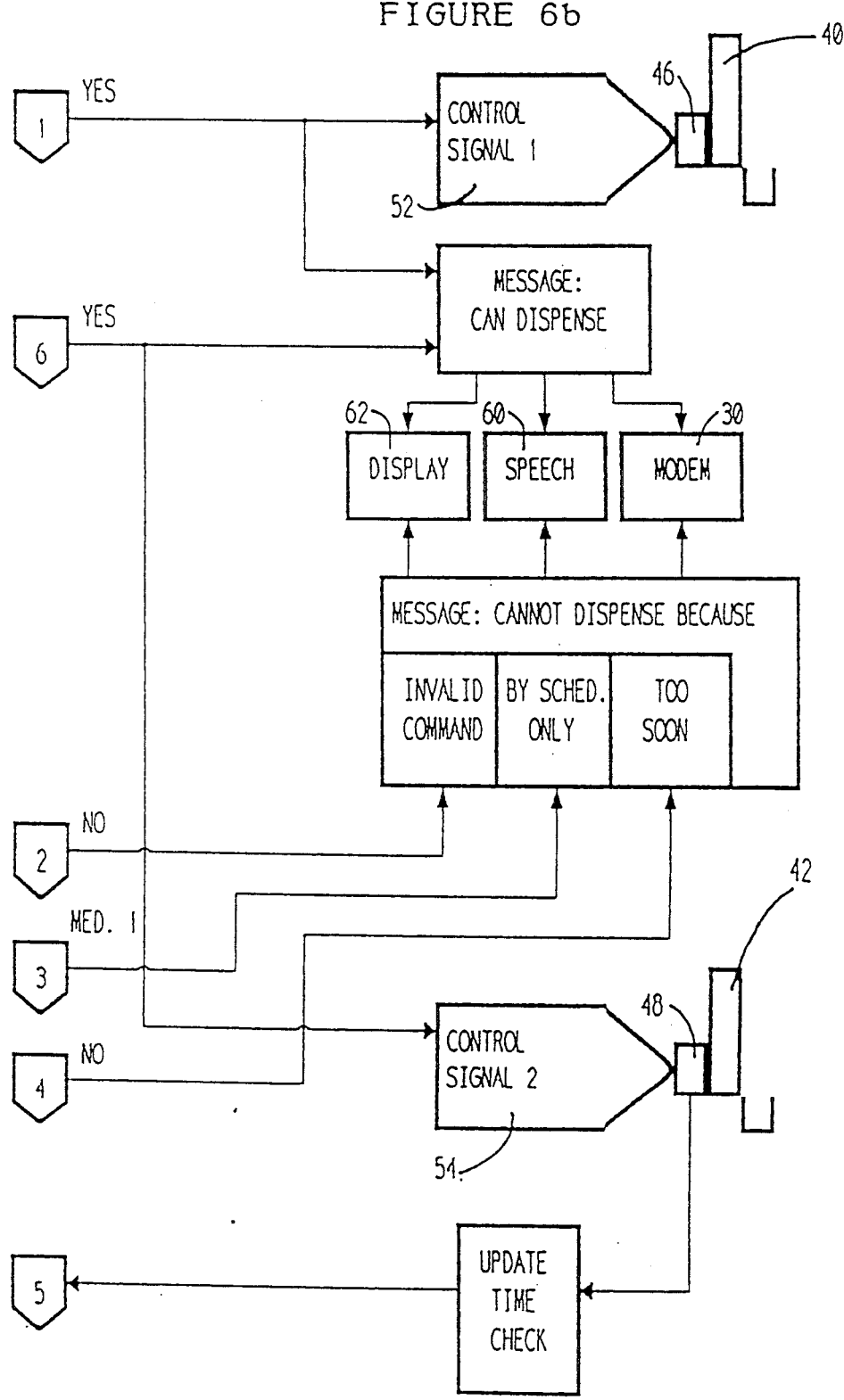

The control element 50 associated with this arrangement is shown diagrammatically in FIG. 6. The prescribed medication schedule is retained in the internal memory 26. The control element 50 includes a first operative sequence 64 that will generate the first control signal 52 upon receiving a valid administer medication command from an internal source (that is, a command generated internally based upon preprogrammed considerations). In the illustrated embodiment, the appropriate administer medication command is internally issued periodically by the CPU 22, based upon a continuous real time monitoring of the prescribed medication schedule stored in the internal memory 26.

Upon generation of the first control signal 52, medication retained in the first storage compartment 40, and only the first storage compartment 40, will be released to the patient.

Preferably, the first operative sequence 64 also generates a "Can Administer" message, using one or more of the output devices (the speech generator 60 and/or the display 62), advising the patient that the prescribed medication is being dispensed according to schedule.

The control element 50 also includes a second operative sequence 66 that, in association with the external input devices (modem 30/key input 58/speech recognition 56), receives and interprets one or more medication delivery commands received from an external source, such as the patient or the central facility 28. As shown in FIG. 6, the second operative sequence 66 conducts a validity check upon the command. The second operative sequence 66 also checks to determine what type or category of medication is being requested.

Upon receipt of a valid command or commands requesting the proper type of medication, the second operative sequence 66 generates the second control signal 54. The medication retained in the second storage compartment 42, but not the first storage compartment 40, is thereby released to the patient.

The second operative sequence 66 also preferably communicates an appropriate "Can Administer" message to the patient through one or more of the output devices 60/62. If the medication request originates from the patient, an advisory message may also be sent to the central facility 28 via the modem 30 at the time an "on demand" request is received and implemented.

If an invalid command is received, or if the patient requests a medication that can only be administered according to an internal command from the internal memory, an appropriate "Cannot Dispense" message is display and/or spoken using the output devices 60/62.

Preferably, whenever a decision is made to either dispense medication or withhold medication, the decision is recorded in internal memory 26 for record keeping purposes.

The first delivery mechanism 46 is thereby actuated in response to an internally generated command signal, but not in response to an externally generated command signal. The first category of medication can thus be safely retained within the first storage compartment 40 away from patient access, except as controlled by the control element 50 (via the first control signal 52). Strict compliance with the prescribed medication schedule is assured.

The second delivery mechanism 48 is actuated in response to the second control signal 54 based upon externally received commands. The second category of "on demand" medication can thus be safely retained in the second storage compartment 42 for administration externally controlled by the patient or the central facility 28 by issuing a proper external command.

In the illustrated and preferred embodiment shown in FIG. 6, the control element 50 also includes a third operative sequence 68 that maintains a real time record of "on demand" administrations of medication and the elapsed time period between them. The third operative sequence 68 includes timing means 70 for comparing the elapsed time between one actuation and the next subsequent actuation command to a prescribed fixed interval. The third operative sequence 68 will, based upon the output of the timing means 70, prevent the next subsequent actuation of the second delivery mechanism 48, despite the receipt of a valid medication command, when the elapsed time period is less than the prescribed period.

In the illustrated and preferred embodiment, the third operative sequence 68 also informs the patient through an appropriate "Cannot Administer" message via one or more of the output devices 60/62. In addition, an advisory message can also be transmitted to the central facility 28 via the modem 30. In this way, the system guards against mismedication or overuse of the "on demand" category of medication.

The specific configuration of the interactive medication delivery system 20 as above described can vary according to the form in which the medication is administered. For example, one or more types of medication can be administered in predetermined dosages in sealed packets or "blister packs". Alternatively, or in combination, single dosages of a medication can be administered in a pill or caplet form, either in unsealed, "loose" form or on sealed rolls.

Attention is directed to FIGS. 1 to 3 and 7 to 13, where a system 200 for storing and delivering individual pills or caplets is shown that embodies the features of the invention.

Figure 3:
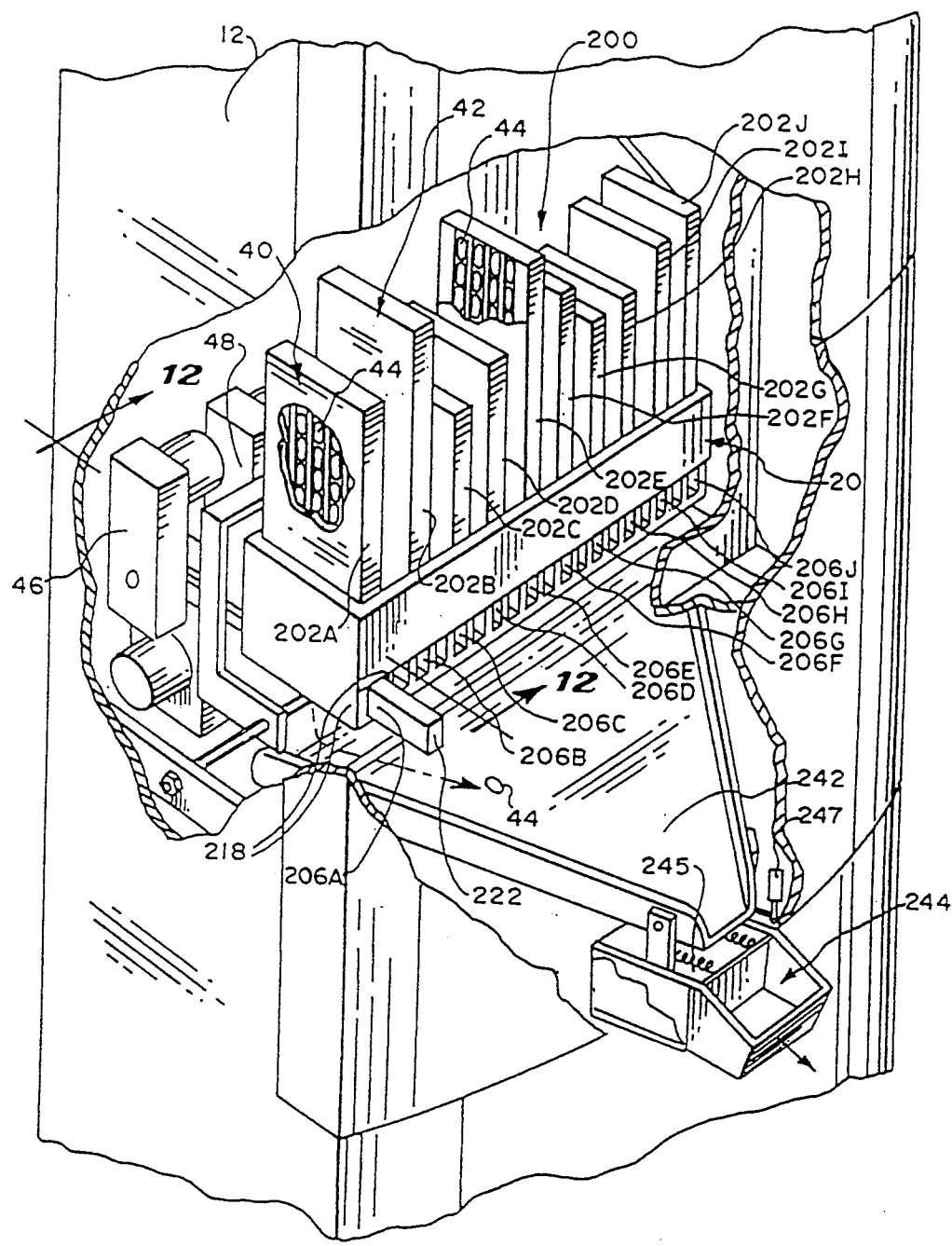
FIG. 3 is an enlarged perspective view, with portions broken away, of the interior of the device shown in FIG. 2, showing the enclosed medication storage and dispensing system.

The system 200, is carried within the confines of the patient monitoring and assistance device 10 (see FIGS. 1 to 3). The system 200 includes a number of housings, each enclosing a discrete medication storage compartment 202 A through J (see FIG. 3). The storage compartments 202 are each capable of separately storing medication in pill or caplet form.

In the illustrated embodiment shown in FIG. 3, there are ten storage compartments 202 A to J. Of course, the number of individual compartments can vary according to the needs of the patient. Each compartment 202 is capable of holding a number of individual pills/caplets (designated by reference numeral 44 in FIG. 3). The number of pills/caplets carried within each compartment 202 is determined by the physician according to the demands of the particular medication regime and how often the medication is to be replenished. Typically, a two week supply of medication can be contained within each compartment 202.

As shown in FIG. 3, the pills/caplets 44 are arranged side-by-side in a plurality of vertically stacked columns 208 within each compartment 202. As shown in FIG. 3, the compartments 202 preferably differ in overall vertical height and/or transverse thickness. The differing physical size of the compartments 202 (particularly in terms of thickness) permits the storage of pills/caplets of differing sizes. It also assures the proper ordered arrangement of the compartments 202 within the system 200, as will be described in greater detail later.

The frame 204 that carries the compartments 202 is mounted in the device 10, behind the drawer 38 that contains the testing devices (see FIGS. 7 and 8). The frame 204 can be tilted out from back of the device 10 for service and to load medication into the system 200 (see FIG. 2 also).

In the illustrated embodiment, as best seen in FIG. 3, the system 200 includes ten separate medication delivery means or mechanisms 206 A through J, one associated with each storage compartment 202. Each mechanism 206 is individually controlled by one of the control elements 50 in response to a prescribed control signal or signals in the manner previously described.

Each delivery mechanism 206 is identical in construction, so only one will be described in detail.

Figure 9:
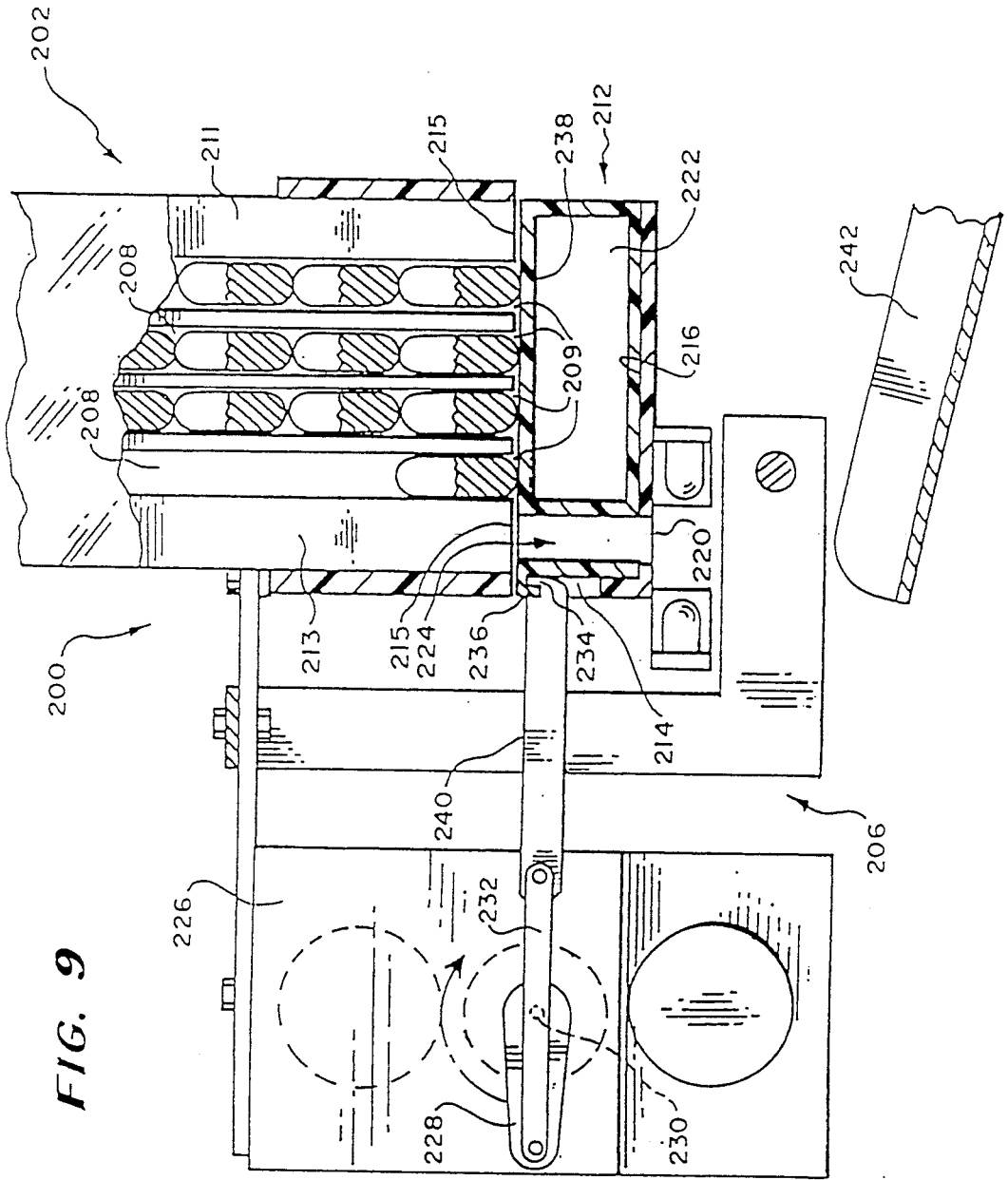
FIGS. 9 to 12 are enlarged side views of the medication delivery system taken generally along line 9—9 in FIG. 3, showing the sequence of operation in dispensing medication in caplet form.
Figure 12:
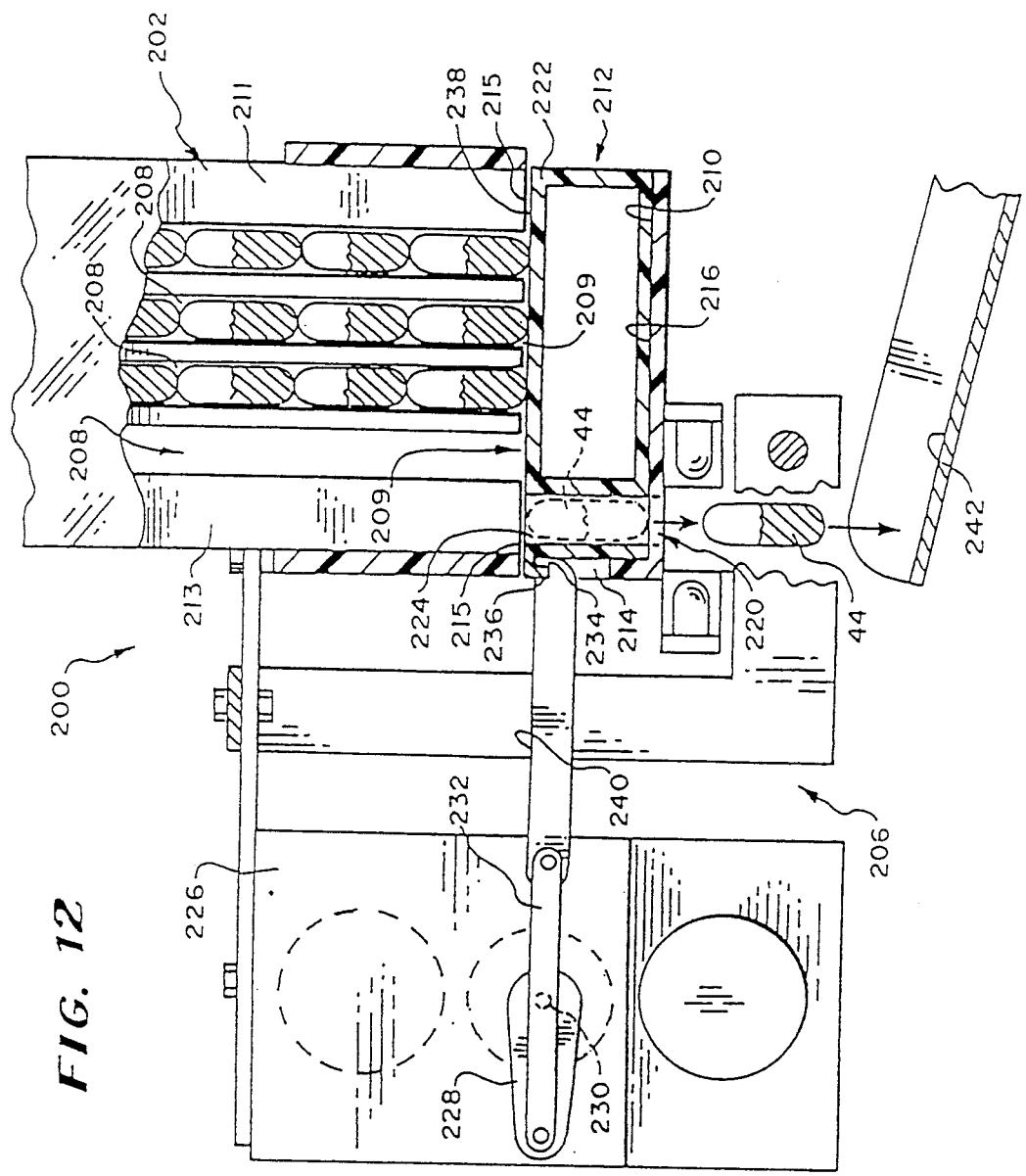

In the illustrated arrangement (as best shown in FIGS. 9 and 12), the medication storage columns 208 are located between a front (right) wall 211 and a rear (left) wall 213 formed within the compartment 202. The lower end 209 of each vertical medication storage column 208 is open. The ends 209 open into a dispensing channel 210 that spans the bottom of the storage compartment 202. The lower edges 215 of the front and rear walls 211 and 213 are closed.

The channel 210 includes an open front end 212 adjacent the compartment's front wall 211 and an open back end 214 adjacent the compartment's rear wall 213 (respectively positioned to the right and to the left in FIGS. 9 and 12). The channel 210 also includes a bottom wall 216 and two upstanding sidewalls 218 (see FIG. 3). The channel bottom wall 216 includes a opening 220 adjacent its open back (left) end 214, directly beneath the closed lower edge 215 of the compartment's rear wall 213.

Figure 11:
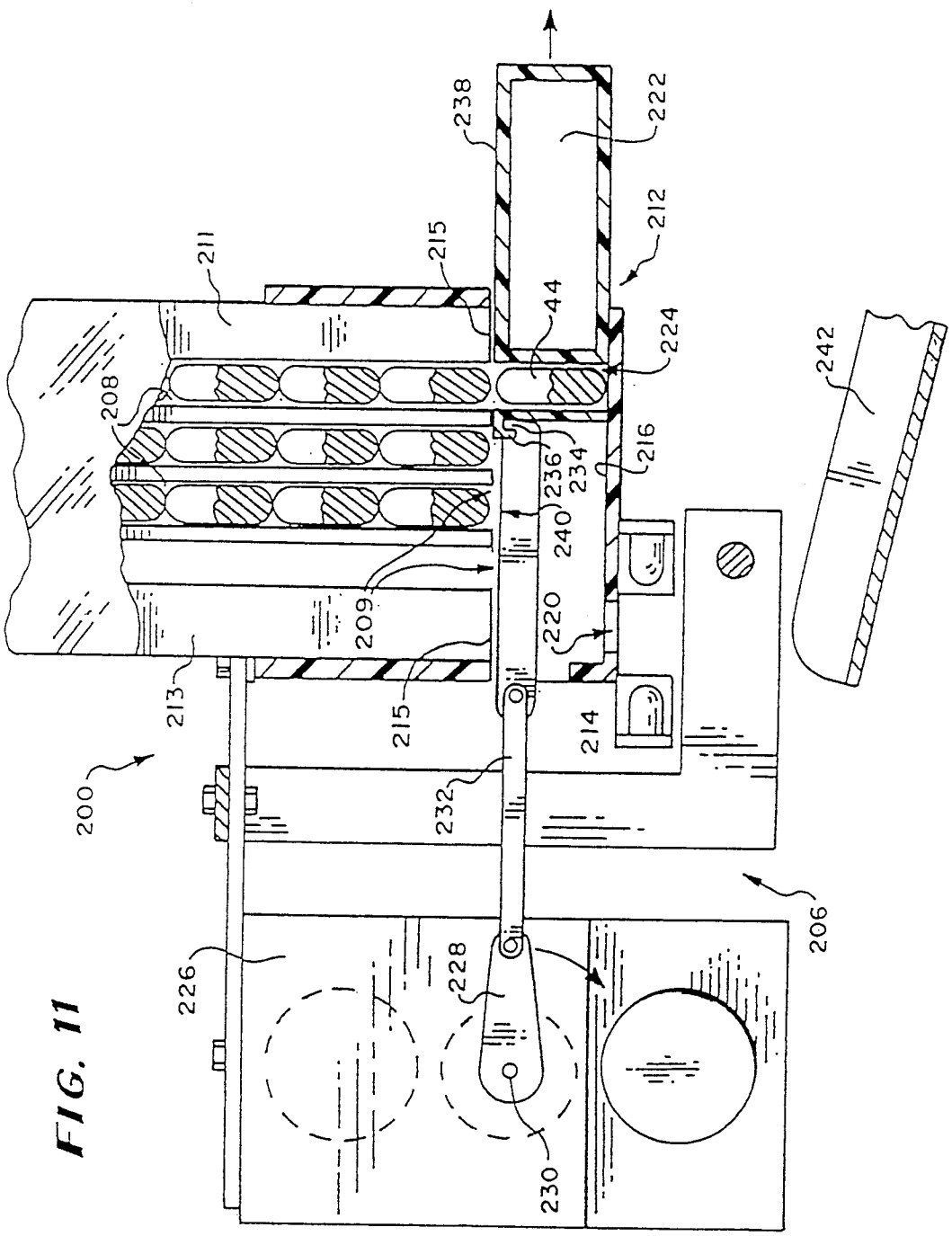

The delivery mechanism includes a shuttle member 222 that is movable within the channel 210 between a first or rearward position, fully within the channel 210 (shown in FIGS. 9 and 12), and a second or forward position, extending partially outside the open front end 212 of the channel 210 (shown in FIG. 11).

Figure 10:
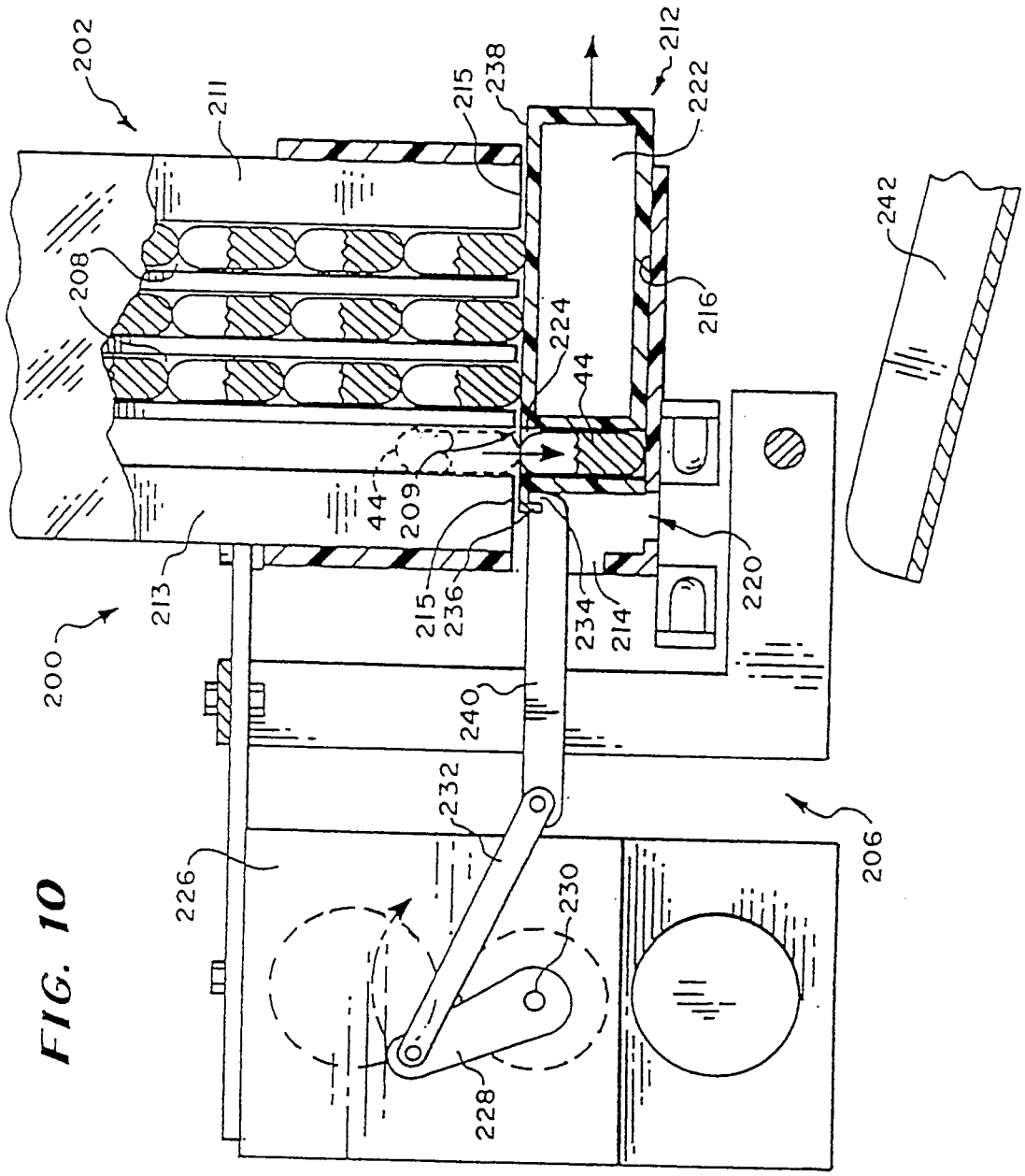

The shuttle member 222 includes an open passageway 224 that registers with the bottom opening 220 in the channel 210 when the shuttle member 222 is in its rearward position (see FIGS. 9 and 12). Movement of the shuttle member 222 successively toward the forward position (as shown in FIGS. 10 and 11) brings the passageway 224 into sequential registration with the open bottom 209 of each of the storage columns 208.

A linkage assembly couples each shuttle member 222 to an associated electric motor 226 to drive the shuttle member 222 laterally forward and backward within the channel 210. While the construction of the linkage assembly may vary, in the illustrated embodiment, it includes a rotating crank 228 coupled to the drive shaft 230 of the associated motor 226. A double pivoted link 232 is attached at one end to the crank 228. The other end of the double pivoted link 232 includes a hook 234 that attaches to a lip 236 on the end wall of the shuttle member 222.

Rotation of crank 228 thereby imparts forward and rearward pivotal movement to the shuttle member 222. In particular, as shown in FIGS. 9 to 12, one full revolution (360-degrees) of the crank 228 will cycle the shuttle member 222 from its rearward position (FIG. 9) into its forward position (FIG. 11) and back to its rearward position (FIG. 12).

As the shuttle member 222 is moved out toward its forward position (see FIG. 10), the passageway 224 will successively come into and out of registry with the bottom 209 of each storage column 208 beginning with the rearwardmost (farthest left) column. The first bottommost pill/caplet encountered in a column will fall by gravity into the empty passageway 224 (as see in FIG. 10). The closed bottom 216 of the channel 210 retains the fallen pill/caplet within the passageway 224 as the shuttle member 222 moves into is fully forward position and back toward its rearward position (in which the passageway is located beneath the closed lower edge 215 of the compartment's rear wall 213). The presence of the retained pill/caplet prevents another pill/caplet from falling into the passageway 224 (as seen in FIG. 11). Likewise, the leading top wall portion 238 of the shuttle member 222 and the trailing top portion 240 of the link 232 serve to progressively close the bottoms of the other columns as the shuttle member 222 is advanced, preventing additional pills/caplets from entering the channel 210.

When the shuttle member 222 returns to the rearward position (see FIG. 12), the passageway 224 will again register with the bottom channel opening 220. The retained pill/caplet will fall from the passageway 224 through the bottom channel opening 220 and then into a delivery chute 242 that leads to a medication dispenser 244 at the front of the device 10 (see FIG. 3 also).

As shown in FIGS. 1 and 2, the medication dispenser 244 is movable between a closed position (FIG. 1) and an opened position (FIGS. 2 and 3). A spring 245 (see FIG. 3) normally biases the dispenser 244 toward the opened position, and a solenoid controlled latching mechanism 247 is provided to lock the dispenser 244 in the closed position. At the time medication is released into the delivery chute 242, the dispenser 244 is located in its locked and closed position. Upon delivery of the medication to the dispenser 244, a signal to the latching mechanism 247 allows the dispenser 244 to move into its opened position in response to the bias of the spring 245. The dispensed medication is thereby made available to the patient. Upon taking the medication, the patient closes the dispenser 244, preferably in response to a prompt generated by the device 200.

As in the previously described embodiment, in the illustrated and preferred embodiment of this system (see FIGS. 7 and 13), each compartment 202 can be individually removed from the housing 204 as a module for replenishment of the medication when the frame 204 is tilted through the back of the device 10. The removable, interchangeable modular design of the compartments 202 simplifies a change in medication brought about by a change in the prescribed medication regime.

Again, it is contemplated that the modular compartments 202 will be prepacked by trained medical or pharmacy personnel at a location away from the device 10 and then carried on site.

In the illustrated arrangement shown in FIG. 13, the motors and linkage assemblies remain in the frame 204 upon removal of the compartments 202. The hooked end 234 of the pivoted link 232 is readily engaged and disengaged from the lip 236 of the associated shuttle member 222.

The housing 204 includes slots 250 arranged to receive and retain the compartments 202 in proper alignment with the associated linkage assembly (see FIG. 13). The slots 250, like the compartments 202, differ in size, so that a given compartment 202 will uniquely physically fit into only a selected one of the slots 250 (as shown by phantom arrows in FIG. 13). This assures the desired ordered arrangement of medication within the dispensing system 200.

In the illustrated and preferred embodiment (see FIG. 13), each compartment 202 is uniquely identified using machine readable code 252. In the illustrated embodiment, the code 252 is readable by an optical scanning system 254 associated with each slot. The code 252 contains information about the medication carried within the associated compartment 202, such as the type of medication, the number of dosages contained, and the patient's name or prescription number. The scanning system 254 reads the code 252 as the compartment 202 is inserted into the appropriate fitted slot 250.

As shown in FIG. 13, the control element 50 for the dispensing system 200 preferably includes a comparator 256 that compares the information sensed by the scanning system 254 with an expected result carried in the main memory 26. If the sensed information is not the expected result—for example, when the medication for the wrong patient is being accidentally loaded into the system 200—an appropriate error message is generated.

The system 200 thus assures, in fail-safe fashion, the placement of the prescribed medication for administration to the patient.

The system 200 shown in the drawings includes the separate medication compartments and ten individually controllable delivery mechanisms, one for each compartment. The system 200 can include any one of the control elements 50 shown in FIGS. 6 to 9. The selected control element 50 serves to individually activate the motors 226 associated with each of the compartments 202 by generating different control signals in response to different input criteria in the manner previously described.

For example, if a medication regime requires the administration of three different pills/caplets according to a prescribed schedule, the control element 50 associated with the system 200 can simultaneously generate a first control signal to each of the delivery mechanisms associated with the particular compartments in which the prescribed pills/caplets are located. The three pills/caplets would therefore be dispensed sequentially or at the same time. The control element 50 could dispense other pills/caplets according to different prescribed schedules, or upon patient demands, upon the issuance of appropriate control signals to the other delivery mechanisms.

The system 200 is thereby capable of storing and coordinating the administration of many different categories of medication in pill or caplet form in accordance with one or more prescribed schedules, upon demand, or upon any other selected administration criteria.

It should be appreciated that all of the medication delivery systems described in this Specification are applicable for use out of association with a patient monitoring and assistance device. The systems can be used in virtually any environment where storage and delivery of selective medications are desired, such as in a hospital, nursing home, or pharmacy. It should also be appreciated that the medication delivery systems described can be actuated and controlled manually, without reliance upon the automated and highly interactive microprocessor controlled systems described in this Specification. Furthermore, each delivery mechanism and associated storage compartment can be used individually as a single unit, as well as in the multiple configurations shown in this Specification.

The features of the many aspects of the invention are set forth in the following claims.

We claim:

1. A medication delivery device for individual pills/caplets comprising a housing including a storage chamber which includes at least two separate storage compartments, each of the compartments capable of holding at least one pill/caplet and a dispensing chamber, each compartment of the storage chamber having a first opening communicating with the dispensing chamber for conveying a pill/caplet from the storage chamber into the dispensing chamber, the dispensing chamber having a second opening for dispensing the pill/caplet from the housing, and a shuttle member movable within the dispensing chamber between a first and second position, the shuttle member having delivery means for receiving a pill/caplet through each of the first openings as the shuttle member is moved from its first position toward its second position and for carrying the received pill/caplet to the second opening for dispensing as the shuttle member is returned to its first position, wherein, as the shuttle member is moved from its first position toward its second position, the delivery means encounters one of the first openings before the other one of the first openings, and wherein the delivery means receives the pill/caplet from the first encountered opening of a compartment that contains a pill/caplet.

2. A medication delivery device according to claim 1 wherein the delivery means includes a passage which registers with the first opening to receive the pill/caplet when the shuttle member is in a predetermined position between the first and second positions and which registers with the second opening to dispense the received pill/caplet from the passage when the shuttle member is in its first position, and wherein the delivery means includes wall means adjacent the passage for blocking the first opening when the shuttle member is spaced from the predetermined position.

3. A medication delivery device according to claim 1 wherein the delivery means receives only one pill/caplet as the shuttle member is moved between its first and second positions, the first received pill/caplet thereby blocking the receipt of additional pills/caplets from subsequently encountered openings.

4. A medication delivery device according to claim 1 wherein the delivery means includes a passage which registers with the first encountered opening when the shuttle member is in a predetermined first position between the first and second positions, which registers with the second encountered opening when the shuttle member is in a predetermined second position between the first and second positions, and which registers with the second opening when the shuttle member is in its first position.

5. A medication delivery device according to claim 4 wherein the delivery means includes wall means adjacent the passage for blocking the second encountered opening when the shuttle member is in its first predetermined position, for blocking the first encountered opening when the shuttle member is in its second predetermined position, and for blocking all first openings when the shuttle member is in its first position.

6. A medication delivery device according to claim 5 wherein the passage accommodates only one pill/caplet as the shuttle member is moved between its first and second positions, the first received pill- /caplet thereby blocking the receipt of additional pills/caplets from subsequently encountered openings.

7. A medication delivery system for individual pills/caplets comprising a housing at least two medication dispensing devices within the housing for dispensing at least two different medications, each dispensing device including a storage chamber for holding at least one pill/caplet and a dispensing chamber, the storage chamber having a first opening communicating with the dispensing chamber for conveying a pill/caplet from the storage chamber into the dispensing chamber, the dispensing chamber having a second opening for dispensing the pill/caplet from the dispensing chamber, and a shuttle member movable within the dispensing chamber between a first and second position, the shuttle member having delivery means for receiving a pill/caplet through the first opening as the shuttle member is moved from its first position toward its second position and for carrying the received pill/caplet to the second opening for dispensing as the shuttle member is returned to its first position, means for independently actuating the shuttle member of each dispensing device, and means for selectively removing and returning each dispensing device from the housing for replenishment and replacement.

8. A medication delivery system comprising a housing, separate first and second dispensing devices within the housing, each of the dispensing devices including storage means for storing at least one dose of a medication within the housing away from access by the user and delivery means associated with the storage means for selectively delivering a medication dose from the associated storage means to the user, at least one of the dispensing devices containing medication in individual pill/caplet form and comprising a storage chamber for holding at least one pill/caplet and a dispensing chamber, the storage chamber having a first opening communicating with the dispensing chamber for conveying a pill/caplet from the storage chamber into the dispensing chamber, the dispensing chamber having a second opening for dispensing the pill/caplet from the dispensing chamber, and a shuttle member movable within the dispensing chamber between a first and second position, the shuttle member having delivery means for receiving a pill/caplet through the first opening as the shuttle member is moved from its first position toward its second position and for carrying the received pill/caplet to the second opening for dispensing as the shuttle member is returned to its first position, and wherein the associated delivery means comprises means for actuating the shuttle member, and system control means associated with the first and second storage means for actuating the delivery means associated with the first storage means in response to a first medication criteria and for actuating the delivery means associated with the second storage means in response to a second medication criteria different from the first medication criteria.

* * * * *